(12) United States Patent
Quinn et al.

(10) Patent No.: US 7,727,538 B2
(45) Date of Patent: *Jun. 1, 2010

(54) METHODS AND COMPOUNDS FOR THE TREATMENT OF MUCUS HYPERSECRETION

(75) Inventors: Conrad Padraig Quinn, Lilburn, GA (US); Keith Alan Foster, Salisbury (GB); John Chaddock, Salisbury (GB)

(73) Assignee: Syntaxin Ltd., Abingdon, Oxfordshire (GB)

( * ) Notice: Subject to any disclaimer, the term of this patent is extended or adjusted under 35 U.S.C. 154(b) by 673 days.

This patent is subject to a terminal disclaimer.

(21) Appl. No.: 11/518,213

(22) Filed: Sep. 11, 2006

(65) Prior Publication Data

US 2007/0010447 A1  Jan. 11, 2007

Related U.S. Application Data

(63) Continuation of application No. 10/633,698, filed on Aug. 5, 2003, now abandoned, which is a continuation-in-part of application No. 09/763,669, filed as application No. PCT/GB99/02806 on Aug. 25, 1999, now Pat. No. 6,632,440.

(30) Foreign Application Priority Data

Aug. 25, 1998 (GB) ................................ 9818548.1

(51) Int. Cl.
*A61K 39/68* (2006.01)
*A61K 39/00* (2006.01)
*C07K 14/00* (2006.01)

(52) U.S. Cl. .................. 424/239.1; 424/236.1; 424/9.1; 514/2; 514/12; 530/350; 435/7.1; 435/6; 435/69.1; 435/325; 435/368; 435/371

(58) Field of Classification Search .............. 424/239.1, 424/9.1, 236.1; 514/2, 12; 530/350; 435/7.1, 435/6, 69.1, 325, 368, 371
See application file for complete search history.

(56) References Cited

U.S. PATENT DOCUMENTS

| | | | |
|---|---|---|---|
| 4,792,447 A | 12/1988 | Uhr et al. | |
| 4,873,346 A | 10/1989 | Anderson | |
| 5,668,255 A | 9/1997 | Murphy | |
| 5,766,605 A | 6/1998 | Sanders et al. | |
| 5,989,545 A | 11/1999 | Foster et al. | |
| 6,395,513 B1 | 5/2002 | Foster et al. | |
| 6,461,617 B1 | 10/2002 | Shone et al. | |
| 6,632,440 B1 | 10/2003 | Quinn et al. | |
| 6,962,703 B2 | 11/2005 | Foster et al. | |
| 7,052,702 B1 | 5/2006 | Duggan et al. | |
| 7,192,596 B2 | 3/2007 | Shone et al. | |
| 2003/0049264 A1 | 3/2003 | Foster et al. | |
| 2003/0147895 A1 | 8/2003 | Shone et al. | |
| 2003/0166238 A1 | 9/2003 | Shone et al. | |

FOREIGN PATENT DOCUMENTS

| | | |
|---|---|---|
| DE | 197 35 105 A1 | 3/1999 |
| EP | 0 673 938 A2 | 9/1995 |
| WO | WO 91/09871 A1 | 7/1991 |
| WO | WO 92/15327 A1 | 9/1992 |
| WO | WO 93/04191 A1 | 3/1993 |
| WO | WO 93/15766 A1 | 8/1993 |
| WO | WO 94/21300 A2 | 9/1994 |
| WO | WO 95/17904 A2 | 7/1995 |
| WO | WO 95/28171 A1 | 10/1995 |
| WO | WO 95/33850 A1 | 12/1995 |
| WO | WO 96/12802 A1 | 5/1996 |
| WO | WO 96/33273 A1 | 10/1996 |
| WO | WO 97/13410 A1 | 4/1997 |
| WO | WO 98/07684 A1 | 2/1998 |
| WO | WO 98/07864 A1 | 2/1998 |
| WO | WO 98/08540 A1 | 3/1998 |
| WO | WO 99/58571 A2 | 11/1999 |
| WO | WO 00/04926 A2 | 2/2000 |
| WO | WO 00/10598 A2 | 3/2000 |

OTHER PUBLICATIONS

Bizzini, B., "Investigation of the Mode of Action of Tetanus Toxin with the Aid of Hybrid Molecules Consisting in Part of Tetanus Toxin-Derived Fragments," *Bacterial Protein Toxins*, pp. 427-434, Academic Press London (1984).
Blaustein, R.O. et al., "The N-terminal half of the heavy chan of botulinum type A neurotoxin forms channels in planar phospholipid bilayers," *FEBS Letters* 226:115-120, Elsevier Science Publishers B.V. (Biomedical Division) (Dec. 1987).
Fisher, C.E., et al., "Genetic construction and properties of a diptheria toxin-related substance P fusion protein: In vitro destruction of cells bearing substance P receptors," *Proc. Natl. Acad. Sci. USA* 93:7341-7345, National Academy of Sciences USA (1996).
Hambleton, P., "*Clostridium botulinum* toxins: a general review of involvement in disease, structure, mode of action and preparation for clinical use," *J. Neurol.* 239:16-20, Springer-Verlag (1992).
Hay, D.W.P., "Chronic obstructive pulmonary disease: emerging therapies," *Current Opinion in Chemical Biology* 4:412-419, Elsevier Science Ltd. (Aug. 2000).
Kielian, M., et al., Mechanisms of Mutations Inhibiting Fusion and Infection by Semliki Forest Virus, *J. Cell Biol.* 134:863-872, The Rockefeller University Press (1996).

(Continued)

*Primary Examiner*—Chih-Min Kam
(74) *Attorney, Agent, or Firm*—Morris, Manning & Martin, LLP; Christopher W. Raimund (57) ABSTRACT

A method of treating mucus hypersecretion, the causative factor in chronic obstructive pulmonary disease (COPD), asthma and other clinical conditions involving COPD, comprises administering a compound that inhibits exocytosis in mucus secreting cells or neurones that control or direct mucus secretion. Also described is a compound, for use in the treatment of hypersecretion of mucus, which inhibits mucus secretion by inhibiting mucus secretion by mucus secreting cells, and/or inhibiting neurotransmitter release from neuronal cells controlling or directing mucus secretion.

21 Claims, 6 Drawing Sheets

OTHER PUBLICATIONS

Kihara, A., and Pastan, I., "Analysis of Sequences Required for the Cytotoxic Action of a Chimeric Toxin Composed of *Pseudomonas* Exotoxin and Transforming Growth Factor α," *Bioconjug. Chem.* 5:532-538, American Chemical Society (1994).

Kurazono, H., et al., "Minimal Essential Domains Specifying Toxicity of the Light Chains of Tetanus Toxin and Botulinum Neurotoxin Type A," *J. Biol. Chem.* 267:14721-14729, American Society for Biochemistry and Molecular Biology, Inc. (1992).

London, E., "Diphtheria toxin: membrane interaction and membrane translocation," *Biochim. Biophys. Acta 1113*:25-51, Elsevier Science Publishers B.V. (1992).

Madison, J.M., and Irwin, R.S., "Chronic obstructive pulmonary disease," *The Lancet* 352:467-473, The Lancet Publishing Group (Aug. 8, 1998).

Murata, M., et al., "pH-Dependent Membrane Fusion and Vesiculation of Phospholipid Large Unilamellar Vesicles Induced by Amphiphilic Anionic and Cationic Peptides," *Biochemistry* 31:1986-1992, American Chemical Society (1992).

Nishiki, T., et al., "Identification of Protein Receptor for *Clostridium botulinum* Type B Neurotoxin in Rat Brain Synaptosomes," *J. Biol. Chem.* 269:10498-10503, American Society for Biochemistry and Molecular Biology, Inc. (1994).

Nishiki, T., et al., "The high-affinity binding of Clostridium botulinum type B neurotoxin to synaptotagmin II associated with gangliosides GT1b/GD1a," *FEBS Lett.* 378:253-257, Federation of European Biochemical Societies (1996).

Poulain, B., et al., "Inhibition of transmitter release by botulinum neurotoxin A. Contributions of various fragments to the intoxication process," *Eur. J. Biochem.* 185:197-203, Federation of European Biochemical Societies (1989).

Picard-Maureau, M., et al., "Foamy Virus Envelope Glycoprotein-Mediated Entry Involves a pH-Dependent Fusion Process," *J. Virol.* 77:4722-4730, American Society for Microbiology (Apr. 2003).

Plank, C., et al., "The Influence of Endosome-disruptive Peptides on Gene Transfer Using Synthetic Virus-like Gene Transfer Systems," *J. Biol. Chem.* 269:12918-12924, The American Society for Biochemistry and Molecular Biology, Inc. (1994).

Prior, T.I., et al., "Translocation Mediated by Domain II of *Pseudomonas* Exotoxin A: Transport of Barnase into the Cytosol," *Biochemistry* 31:3555-3559, American Chemical Society (1992).

Rogers, D.F., "Motor control of airway goblet cells and glands," *Respiration Physiology* 125:129-144, Elsevier Science B.V. (Mar. 2001).

Rogers, D.F., "Pharmacological regulation of the neuronal control of airway mucus secretion," *Current Opinion in Pharmacology* 2:249-255, Elsevier Science Ltd. (Jun. 2002).

Seth, S., et al., "Activation of Fusion by the SER Virus F Protein: a Low-pH-Dependent Paramyxovirus Entry Process," *J. Virol.* 77:6520-6527, American Society for Microbiology (Jun. 2003).

Shone et al., "Delivery of Superoxide Dismutase to Neuronal Cells," U.S. Appl. No. 11/062,471, filed Feb. 22, 2005.

Shone et al., "Recombinant Toxin Fragments," U.S. Appl. No. 11/077,550, filed Mar. 11, 2005.

Shone et al., "Recombinant Toxin Fragments," U.S. Appl. No. 10/527,411, filed Mar. 11, 2005.

Shone et al., "Recombinant Toxin Fragments," U.S. Appl. No. 11/644,010, filed Dec. 22, 2006.

Shone, C.C. et al., "A 50-kDa fragment from the $NH_2$-terminus of the heavy subunit of *Clostridium botulinum* type A neurotoxin forms channels in lipid vesicles," *Eur. J. Biochem.* 167:175-180, Springer International (Aug. 17, 1987).

Silverman, J.A., et al., "Mutational Analysis of the Helical Hairpin Region of Diphtheria Toxin Transmembrane Domain," *J. Biol. Chem.* 269:22524-22532, American Society for Biochemistry and Molecular Biology, Inc. (1994).

Wagner, E., et al., "Influenza virus hemagglutinin HA-2 N-terminal fusogenic peptides augment gene transfer by transferrin-polylysine-DNA complexes: Toward a synthetic virus-like gene-transfer vehicle," *Proc. Natl. Acad. Sci. USA* 89:7934-7938, National Academy Press (1992).

Yao, Y., et al., "Membrane fusion activity of vesicular stomatitis virus glycoprotein G is induced by low pH but not by heat or denaturant," *Virology* 310:319-332, Academic Press (Jun. 2003).

Zhou, L., et al., "Expression and purification of the Light Chain of Botulinum Neurotoxin A: A Single Mutation Abolishes Its Cleavage of SNAP-25 and Neurotoxicity after Reconstitution with the Heavy Chain," *Biochemistry* 34:15175-15181, American Chemical Society (1995).

Office Action for U.S. Appl. No. 10/633,698, Quinn, C.P., filed Aug. 5, 2003, mailed on Apr. 29, 2005.

Office Action for U.S. Appl. No. 10/633,698, Quinn, C.P., filed Aug. 5, 2003, mailed on Oct. 18, 2005.

Office Action for U.S. Appl. No. 10/633,698, Quinn, C.P., filed Aug. 5, 2003, mailed on May 9, 2006.

Application and Prosecution History for "Recombinant Toxin Fragments," Shone et al., U.S. Appl. No. 09/255,829, filed Feb. 23, 1999.

Application and Prosecution History for "Conjugates of Galatose-Binding Lectins and Clostridial Neurotoxins as Analgesics," Duggan et al., U.S. Appl. No. 09/529,130, with a §371 date Jun. 22, 2000.

Application and Prosecution History for "Methods and Compounds for the Treatment of Mucus Hypersecretion," Quinn et al., U.S. Appl. No. 09/763,669, with a §371 date May 29, 2001.

Application and Prosecution History for "Delivery of Superoxide Dismutase to Neuronal Cells," Shone et al., U.S. Appl. No. 09/831,050, with a §371 date of Aug. 20, 2001.

Application and Prosecution History for "Constructs for Delivery of Therapeutic Agents to Neuronal Cells," Shone et al., U.S. Appl. No. 10/130,973, with a §371 date of Jun. 25, 2002.

Application and Prosecution History for "Recombinant Toxin Fragments," Shone et al., U.S. Appl. No. 10/241,596, filed Sep. 12, 2002.

Database—12, English language abstract of DE 197 35 105 A1, at esp@cenet.

Dialog File 351, Accession No. 2000-072332, Derwent WPI English language abstract for WO 99/58571.

International Search Report for PCT/GB99/02806, mailed Mar. 16, 2000.

Inhibition of Release (%) vs. Concentration of Agent (μg/ml)

● WGA-LH$_N$/A    ○ LH$_N$/A

Fig. 5

Inhibition of Release (%) vs. Concentration of Agent (μg/ml)

● WGA-LH$_N$/A    ○ LH$_N$/A

Fig. 6

Inhibition of Release (%) vs Concentration of Agent (µg/ml)

● WGA-LH$_N$/A    ○ LH$_N$/A

Fig. 7

SEQUENCE LISTING

```
<160> NUMBER OF SEQ ID NOS: 8

<210> SEQ ID NO 1
<211> LENGTH: 23
<212> TYPE: PRT
<213> ORGANISM: Influenza virus

<400> SEQUENCE: 1

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 2
<211> LENGTH: 12
<212> TYPE: PRT
```

```
<213> ORGANISM: Unknown
<220> FEATURE:
<223> OTHER INFORMATION: Substance P peptide sequence

<400> SEQUENCE: 2

Arg Pro Lys Pro Gln Gln Phe Phe Gly Leu Met Cys
1               5                   10

<210> SEQ ID NO 3
<211> LENGTH: 12
<212> TYPE: PRT
<213> ORGANISM: Unknown
<220> FEATURE:
<223> OTHER INFORMATION: Substance P peptide sequence with N-terminal
      Cys

<400> SEQUENCE: 3

Cys Arg Pro Lys Pro Gln Gln Phe Phe Gly Leu Met
1               5                   10

<210> SEQ ID NO 4
<211> LENGTH: 4
<212> TYPE: PRT
<213> ORGANISM: Unknown
<220> FEATURE:
<223> OTHER INFORMATION: Factor Xa
<220> FEATURE:
<221> NAME/KEY: MISC_FEATURE
<222> LOCATION: (4)..(4)
<223> OTHER INFORMATION: specific cleavable peptide bond

<400> SEQUENCE: 4

Ile Glu Gly Arg
1

<210> SEQ ID NO 5
<211> LENGTH: 5
<212> TYPE: PRT
<213> ORGANISM: Unknown
<220> FEATURE:
<223> OTHER INFORMATION: Enterokinase
<220> FEATURE:
<221> NAME/KEY: MISC_FEATURE
<222> LOCATION: (5)..(5)
<223> OTHER INFORMATION: specific cleavable peptide bond

<400> SEQUENCE: 5

Asp Asp Asp Asp Lys
1               5

<210> SEQ ID NO 6
<211> LENGTH: 8
<212> TYPE: PRT
<213> ORGANISM: Unknown
<220> FEATURE:
<223> OTHER INFORMATION: TEV protease
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(8)
<223> OTHER INFORMATION: specific cleavable peptide bond

<400> SEQUENCE: 6
```

```
-continued

Glu Xaa Xaa Tyr Xaa Gln Ser Gly
1               5

<210> SEQ ID NO 7
<211> LENGTH: 8
<212> TYPE: PRT
<213> ORGANISM: Unknown
<220> FEATURE:
<223> OTHER INFORMATION: Precission
<220> FEATURE:
<221> NAME/KEY: MISC_FEATURE
<222> LOCATION: (6)..(7)
<223> OTHER INFORMATION: specific cleavable peptide bond

<400> SEQUENCE: 7

Leu Glu Val Leu Phe Gln Gly Pro
1               5

<210> SEQ ID NO 8
<211> LENGTH: 6
<212> TYPE: PRT
<213> ORGANISM: Unknown
<220> FEATURE:
<223> OTHER INFORMATION: Thrombin
<220> FEATURE:
<221> NAME/KEY: MISC_FEATURE
<222> LOCATION: (4)..(5)
<223> OTHER INFORMATION: specific cleavable peptide bond

<400> SEQUENCE: 8

Leu Val Pro Arg Gly Ser
1               5
```

METHODS AND COMPOUNDS FOR THE TREATMENT OF MUCUS HYPERSECRETION

This Application is Continuation of U.S. patent application Ser. No. 10/633,698, filed Aug. 5, 2003, abandoned, which is a continuation-in-part of U.S. patent application Ser. No. 09/763,669, filed on May 29, 2001, now U.S. Pat. No. 6,632,440, which is a national stage entry of International Application No. PCT/GB99/02806, filed on Aug. 25, 1999.

BACKGROUND OF THE INVENTION

1. Field of the Invention

The present invention relates to treatment of mucus hypersecretion, to compositions therefor and manufacture of those compositions. The present invention relates particularly, though not exclusively, to the treatment of chronic bronchitis in chronic obstructive pulmonary disease (COPD), asthma and other clinical conditions involving COPD.

2. Description of Related Art

Mucus is a thin film of protective viscoelastic liquid which lines the airways. It is a 1-2% aqueous solution, in which the major components are the glycoconjugates known as mucins. Mucus, including the mucins, is secreted by mucus secretory cells, the surface epithelial goblet cells of the large airways and the mucus cells of the submucosal glands. Mucin release occurs by three mechanisms: constitutive secretion, regulated secretion and protease cell surface activity. Of these it is regulated secretion that responds to external stimuli and is amenable to therapeutic intervention in COPD and asthma. Regulated secretion involves release from intracellular granules by docking and fusion of the granules with the cell exterior to release their contents onto the airway surface. Fusion of the granules can either be with the plasma membrane of the epithelial cell or with the membrane of other granules leading to release via multigranular complexes fused at the cell surface. Regulated secretion of mucins is controlled by humoral factors and by neural mechanisms. The neural mechanisms in humans involve a minor contribution from the adrenergic, sympathetic pathway and a major cholinergic, parasympathetic component. Another important neural pathway regulating mucin secretion, particularly the hypersecretion of pathological conditions, is that of the Non-Adrenergic Non-Cholinergic (NANC) pathway. The NANC component involves both an orthodromic pathway involving neuropeptide and nonpeptide transmitters, and a local sensory efferent pathway involving antidromic fibres from sensory C fibres.

COPD is a common respiratory condition, being the fourth most common cause of death in middle age in the Western world. COPD comprises two related diseases, which usually occur together, emphysema and chronic bronchitis. The pathological basis of chronic bronchitis is mucus hypersecretion. The excessive, chronic bronchial secretion results in expectoration, and can last from a few days to many years. The mucus hypersecretion of COPD results in small airway obstruction producing reduced maximal respiratory flow and slow forced lung emptying. There is minimal reversal of the impaired airway function of COPD by bronchodilators and currently no effective therapy for the mucus hypersecretion.

Mucus hypersecretion is also a significant contributing factor to the pathophysiology of asthma. It is a key component in status asthmaticus, and contributes to the chronic symptoms and morbidity of asthma. The mucus hypersecretion component of asthma is not well controlled by current therapies, particularly in severe and chronic cases.

It would accordingly be desirable to treat, reduce or prevent the mucus hypersecretion that causes or leads to these disease conditions.

SUMMARY OF THE INVENTION

Accordingly, the invention provides a method of treating mucus hypersecretion comprising inhibiting mucus secretion by mucus secreting cells and/or inhibiting neurotransmitter release from neuronal cells that control or direct mucus secretion. The invention further provides, in a second aspect, a compound, for use in the treatment of mucus hypersecretion, which inhibits mucus secretion by (i) inhibiting mucus secretion by mucus secreting cells, or (ii) inhibiting neurotransmitter release from neuronal cells controlling or directing mucus secretion.

An advantage of the invention is that an agent for effective treatment of mucus hypersecretion and associated disease states is now provided and used, offering a relief to sufferers where hitherto there was no such agent available.

The present invention thus represents a new different approach to treatment of mucus hypersecretion by inhibiting secretory processes, namely one or other or both of the mucus secretion by mucus secretory cells and the secretion of neurotransmitters regulating mucus secretion. Agents of the present invention reduce mucus secretion and/or prevent the hypersecretion of COPD and asthma, and any other disease in which mucus hypersecretion is a causative element.

DETAILED DESCRIPTION OF THE INVENTION

A compound of the invention typically inhibits exocytosis in mucus secreting cells or neurones that control or direct mucus secretion. This compound is administered to a patient suffering from mucus hypersecretion and inhibition of exocytosis in the cells specified results in reduction of secretion of mucus. Specific disease states caused by or exacerbated by hypersecretion are localised to the airways, and hence an embodiment of the invention comprises topical administration to the airways or to a selected region or to a selected portion of the airways of a compound that inhibits exocytosis in mucus secreting cells or in neurones that control or direct mucus secretion.

A compound of embodiments of the invention is a polypeptide that consists of or comprises an inhibiting domain which inhibits exocytosis in the mucus secreting cell or inhibits exocytosis in a neuronal cell, thereby directly inhibiting exocytosis of mucus or one or more mucus components or indirectly inhibiting mucus secretion by inhibiting exocytosis of neurotransmitter which would in turn lead to or otherwise stimulate mucus secretion. The inhibiting domain can suitably comprise a light chain of a clostridial neurotoxin, or a fragment or variant thereof which inhibits exocytosis.

The compound preferably further comprises a translocating domain that translocates the inhibiting domain into the cell. This domain may comprise a $H_N$ region of a botulinum polypeptide, or a fragment or variant thereof that translocates the inhibiting domain into the cell.

The compound preferably comprises a targeting domain which binds to (i) a mucus secreting cell, or (ii) a neuronal cell controlling or directing mucus secretion. The compound is thus rendered specific for these cell types. It is also optional for the compound to be relatively non-specific but for inhibition of mucus secretion to be achieved via targeting of the compound through choice of route of administration—the compound is hence preferably administered to mucus secreting epithelial cells in the airways, specifically in the lungs.

Whilst a non-specific compound of the invention may affect exocytosis in many cells of a wide range of types, generally only those cells that are stimulated will be affected and these stimulated cells will in typical disease states be those that are secreting mucus and contributing to disease.

When present, suitable targeting domains include, but are not restricted to, a domain selected from Substance P, VIP, beta$_2$ adrenoreceptor agonists, gastrin releasing peptide and calcitonin gene related peptide. The precise cells targeted in preferred embodiments of the invention are selected from (a) cells that secrete mucins, such as epithelial goblet cells and submucosal gland mucus secreting cells, (b) cells that secrete aqueous components of mucus, such as Clara cells and serous cells, and (c) cells that control or direct mucus secretion, such as "sensory-efferent" C-fibres, or NANC neural system fibres. The compound may be administered as a substantially pure preparation all targeted to the same cell type, or may be a mixture of compounds targeted respectively to different cells.

The compound of specific embodiments of the invention comprises first, second and third domains. The first domain is adapted to cleave one or more vesicle or plasma-membrane associated proteins essential to exocytosis. This domain prevents exocytosis once delivered to a targeted cell. The second domain translocates the compound into the cell. This domain delivers the first domain into the cell. The third domain binds to the target cell, ie binds to (i) a mucus secreting cell, or (ii) a neuronal cell controlling or directing mucus secretion, and may be referred to as a targeting moiety ("TM"). The compound may be derived from a toxin and it is preferred that such a compound is free of clostridial neurotoxin and free of any clostridial neurotoxin precursor that can be converted into toxin. Botulinum and tetanus toxin are suitable sources of domains for the compounds of the invention.

In use, the agent of specific embodiments of the invention has a number of discrete functions. It binds to a surface structure (the Binding Site {BS}) which is characteristic of, and has a degree of specificity for, the relevant secretory cells and or neurones in the airways responsible for secretion of mucus and or regulation of said secretion. It enters the cell to which it binds by a process of endocytosis. Only certain cell surface BSs can undergo endocytosis, and preferably the BS to which the agent binds is one of these. The agent enters the cytosol, and modifies components of the exocytotic machinery present in the relevant secretory cells and or neurones in the airways responsible for secretion of mucus and or regulation of said secretion.

Surprisingly, agents of the present invention for treatment of mucus hypersecretion can be produced by modifying a clostridial neurotoxin or fragment thereof. The clostridial neurotoxins share a common architecture of a catalytic L-chain (LC, ca 50 kDa) disulphide linked to a receptor binding and translocating H-chain (HC, ca 100 kDa). The HC polypeptide is considered to comprise all or part of two distinct functional domains. The carboxy-terminal half of the HC (ca 50 kDa), termed the $H_C$ domain, is involved in the high affinity, neurospecific binding of the neurotoxin to cell surface receptors on the target neuron, whilst the amino-terminal half, termed the $H_N$ domain (ca 50 kDa), is considered to mediate the translocation of at least some portion of the neurotoxin across cellular membranes such that the functional activity of the LC is expressed within the target cell. The $H_N$ domain also has the property, under conditions of low pH, of forming ion-permeable channels in lipid membranes, this may in some manner relate to its translocation function.

For botulinum neurotoxin type A (BoNT/A) these domains are considered to reside within amino acid residues 872-1296 for the $H_C$, amino acid residues 449-871 for the $H_N$ and residues 1-448 for the LC. Digestion with trypsin effectively degrades the $H_C$ domain of the BoNT/A to generate a non-toxic fragment designated L $H_N$, which is no longer able to bind to and enter neurons. The $LH_N$ fragment so produced also has the property of enhanced solubility compared to both the parent holotoxin and the isolated LC.

It is therefore possible to provide functional definitions of the domains within the neurotoxin molecule, as follows:

(A) clostridial neurotoxin light chain:

A metalloprotease exhibiting high substrate specificity for vesicle and/or plasma membrane associated proteins involved in the exocytotic process. In particular, it cleaves one or more of SNAP-25, VAMP (synaptobrevin/cellubrevin) and syntaxin.

(B) clostridial neurotoxin heavy chain $H_N$ domain:

A portion of the heavy chain which enables translocation of that portion of the neurotoxin molecule such that a functional expression of light chain activity occurs within a target cell.

The domain responsible for translocation of the endopeptidase activity, following binding of neurotoxin to its specific cell surface receptor via the binding domain, into the target cell.

The domain responsible for formation of ion-permeable pores in lipid membranes under conditions of low pH.

The domain responsible for increasing the solubility of the entire polypeptide compared to the solubility of light chain alone.

(C) clostridial neurotoxin heavy chain $H_C$ domain.

A portion of the heavy chain which is responsible for binding of the native holotoxin to cell surface receptor(s) involved in the intoxicating action of clostridial toxin prior to internalisation of the toxin into the cell.

The identity of the cellular recognition markers for these toxins is currently not understood and no specific receptor species have yet been identified although Kozaki et al. have reported that synaptotagmin may be the receptor for botulinum neurotoxin type B. It is probable that each of the neurotoxins has a different receptor.

By covalently linking a clostridial neurotoxin, or a hybrid of two clostridial neurotoxins, in which the $H_C$ region of the H-chain has been removed or modified, to a new molecule or moiety, the Targeting Moiety (TM), that binds to a BS on the surface of the relevant secretory cells and or neurones in the airways responsible for secretion of mucus and or regulation of said secretion, a novel agent capable of inhibiting mucus secretion is produced. A further surprising aspect of the present invention is that if the L-chain of a clostridial neurotoxin, or a fragment of the L-chain containing the endopeptidase activity, is covalently linked to TM which can also effect internalisation of the L-chain, or a fragment of the L-chain containing the endopeptidase activity, into the cytoplasm of the relevant secretory cells and or neurones in the airways responsible for secretion of mucus and or regulation of said secretion, this also produces a novel agent capable of inhibiting mucus secretion.

Accordingly, the invention may thus provide a compound containing a first domain equivalent to a clostridial toxin light chain and a second domain providing the functional aspects of the $H_N$ of a clostridial toxin heavy chain, whilst lacking the functional aspects of a clostridial toxin $H_C$ domain, and a third domain which binds to the target mucus secreting or mucus secretion controlling cell.

For the purposes of the invention, the functional property or properties of the $H_N$ of a clostridial toxin heavy chain that are to be exhibited by the second domain of the polypeptide of the invention is translocation of the first domain into a target cell once the compound is proximal to the target cell. References hereafter to a $H_N$ domain or to the functions of a $H_N$ domain are references to this property or properties. The second domain is not required to exhibit other properties of the $H_N$ domain of a clostridial toxin heavy chain. A second domain of the invention can thus be relatively insoluble but retain the translocation function of a native toxin—this is of use if solubility is not essential to its administration or if necessary solubility is imparted to a composition made up of that domain and one or more other components by one or more of said other components.

The translocating domain may be obtained from a microbial protein source, in particular from a bacterial or viral protein source. It is well documented that certain domains of bacterial toxin molecules are capable of forming such pores. It is also known that certain translocation domains of virally expressed membrane fusion proteins are capable of forming such pores. Such domains may be employed in the present invention.

Hence, in one embodiment, the translocating domain is a translocating domain of an enzyme, such as a bacterial or viral toxin. One such molecule is the heavy chain of a clostridial neurotoxin, for example botulinum neurotoxin type A. Other sources of bacterial toxin translocating domains include diphtheria toxin and domain II of pseudomonas exotoxin.

Other sources of translocating domains include certain translocating domains of virally expressed membrane fusion proteins. For example, Wagner et al. (1992) and Murata et al. (1992) describe the translocation (i.e. membrane fusion and vesiculation) function of a number of fusogenic and amphiphilic peptides derived from the N-terminal region of influenza virus haemagglutinin. Other virally expressed membrane fusion proteins known to have the desired translocating activity are a translocating domain of a fusogenic peptide of Semliki Forest Virus (SFV), a translocating domain of vesicular stomatitis virus (VSV) glycoprotein G, a translocating domain of SER virus F protein and a translocating domain of Foamy virus envelope glycoprotein. Virally encoded "spike proteins" have particular application in the context of the present invention, for example, the E1 protein of SFV and the G protein of the G protein of VSV.

Preferably it has been found to use only those portions of the protein molecule capable of pore-formation within the endosomal membrane.

Methodology to enable assessment of membrane fusion and thus identification of translocation domains suitable for use in the present invention are provided by Methods in Enzymology Vol 220 and 221, Membrane Fusion Techniques, Parts A and B, Academic Press 1993.

Examples of preferred translocating domains for use in the present invention are listed in the table below. The below-listed citations are all herein incorporated by reference.

| Translocation domain source | Amino acid residues | References |
| --- | --- | --- |
| Diphtheria toxin | 194-380 | Silverman et al., 1994, J. Biol. Chem. 269, 22524-22532 London E., 1992, Biochem. Biophys. Acta., 1113, 25-51 |
| Domain II of pseudomonas exotoxin | 405-613 | Prior et al., 1992, Biochemistry 31, |

-continued

| Translocation domain source | Amino acid residues | References |
| --- | --- | --- |
| | | 3555-3559 Kihara & Pastan, 1994, Bioconj Chem. 5, 532-538 |
| Influenza virus haemagglutinin | GLFGAIAGFIENGW EGMIDGWYG (SEQ ID NO: 1), and variants thereof | Plank et al., 1994, J. Biol. Chem. 269, 12918-12924 Wagner et al, 1992, PNAS, 89, 7934-7938 Murata et al., 1992, Biochemistry 31, 1986-1992 |
| Semliki Forest virus fusogenic protein | Translocation domain | Kielian et al., 1996, J Cell Biol. 134(4), 863-872 |
| Vesicular Stomatitis virus glycoprotein G | 118-139 | Yao et al., 2003, Virology 310(2), 319-332 |
| SER virus F protein | Translocation domain | Seth et al., 2003, J Virol 77(11) 6520-6527 |
| Foamy virus envelope glyoprotein | Translocation domain | Picard-Maureau et al., 2003, J Virol. 77(8), 4722-4730 |

Use of the translocating domains listed in the above table includes use of sequence variants thereof. A variant may comprise one or more conservative nucleic acid substitutions and/or nucleic acid deletions or insertions, with the proviso that the variant possesses the requisite translocating function. A variant may also comprise one or more amino acid substitutions and/or amino acid deletions or insertions, so long as the variant possesses the requisite translocating function.

The only functional requirement of the translocating domain is that it is capable of forming appropriate pores in the endosomal membrane. A number of routine methods are available for confirming that a particular translocating domain has the requisite translocating activity, and thus to determine the presence of a translocating domain. Shone et al. (1987), and Blaustein et al. (1987) provide details of two very simple assays to confirm that any particular bacterial translocating domain has the requisite translocating activity. Shone (1987) describes a simple in vitro assay employing liposomes, which are challenged with a test molecule. The presence of a molecule having the requisite translocating function is confirmed by release from the liposomes of K+ and/or labelled AND. Blaustein (1987) describes a simple in vitro assay employing planar phospholipid bilayer membranes, which are challenged with a test molecule. The presence of a molecule having the requisite translocation function is confirmed by an increase in conductance across the phospholipid membrane.

The polypeptide of the invention may be obtained by expression of a recombinant nucleic acid, preferably a DNA, and is a single polypeptide, that is to say not cleaved into separate light and heavy chain domains. The polypeptide is thus available in convenient and large quantities using recombinant techniques.

The first domain optionally comprises a fragment or variant of a clostridial toxin light chain. The fragment is optionally an N-terminal, or C-terminal fragment of the light chain, or is an internal fragment, so long as it substantially retains the ability to cleave the vesicle or plasma-membrane associated protein essential to exocytosis. Domains necessary for the activity of the light chain of clostridial toxins are described in J. Biol. Chem., Vol. 267, No. 21, Jul. 1992, pages 14721-14729. The variant has a different peptide sequence from the light chain or from the fragment, though it too is capable of cleaving the vesicle or plasma-membrane associated protein. It is conveniently obtained by insertion, deletion and/or substitution of a light chain or fragment thereof. In embodiments of the invention described below a variant sequence comprises (i) an N-terminal extension to a clostridial toxin light chain or fragment (ii) a clostridial toxin light chain or fragment modified by alteration of at least one amino acid (iii) a C-terminal extension to a clostridial toxin light chain or fragment, or (iv) combinations of 2 or more of (i)-(iii).

In an embodiment of the invention described in an example below, the toxin light chain and the portion of the toxin heavy chain are of botulinum toxin type A. In a further embodiment of the invention described in an example below, the toxin light chain and the portion of the toxin heavy chain are of botulinum toxin type B. The polypeptide optionally comprises a light chain or fragment or variant of one toxin type and a heavy chain or fragment or variant of another toxin type.

In a polypeptide according to the invention said second domain preferably comprises a clostridial toxin heavy chain $H_N$ portion or a fragment or variant of a clostridial toxin heavy chain $H_N$ portion. The fragment is optionally an N-terminal or C-terminal or internal fragment, so long as it retains the function of the $H_N$ domain. Teachings of regions within the $H_N$ responsible for its function are provided for example in Biochemistry 1995, 34, pages 15175-15181 and Eur. J. Biochem, 1989, 185, pages 197-203. The variant has a different sequence from the $H_N$ domain or fragment, though it too retains the function of the $H_N$ domain. It is conveniently obtained by insertion, deletion and/or substitution of a $H_N$ domain or fragment thereof. In embodiments of the invention, described below, it comprises (i) an N-terminal extension to a $H_N$ domain or fragment, (ii) a C-terminal extension to a $H_N$ domain or fragment, (iii) a modification to a $H_N$ domain or fragment by alteration of at least one amino acid, or (iv) combinations of 2 or more of (i)-(iii). The clostridial toxin is preferably botulinum toxin or tetanus toxin.

These polypeptides of the invention thus typically contain two or more polypeptide first and second domain, linked by di-sulphide bridges into composite molecules, and further linked to a third domain.

The TM provides specificity for the BS on the relevant neuronal and or secretory cells responsible for secretion of mucus in the airways. The TM component of the agent can comprise one of many cell binding molecules, including, but not limited to, antibodies, monoclonal antibodies, antibody fragments (Fab, F(ab)'$_2$, Fv, ScFv, etc.), lectins, hormones, cytokines, growth factors or peptides.

It is known in the art that the $H_C$ portion of the neurotoxin molecule can be removed from the other portion of the H-chain, known as $H_N$, such that the $H_N$ fragment remains disulphide linked to the L-chain of the neurotoxin providing a fragment known as $LH_N$. Thus, in one embodiment of the present invention the $LH_N$ fragment of a clostridial neurotoxin is covalently linked, using linkages which may include one or more spacer regions, to a TM.

The $H_C$ domain of a clostridial neurotoxin may be mutated or modified, eg by chemical modification, to reduce or preferably incapacitate its ability to bind the neurotoxin to receptors at the neuromuscular junction. This modified clostridial neurotoxin is then covalently linked, using linkages which may include one or more spacer regions, to a TM.

The heavy chain of a clostridial neurotoxin, in which the $H_C$ domain is mutated or modified, eg by chemical modification, to reduce or preferably incapacitate its ability to bind the neurotoxin to receptors at the neuromuscular junction, may be combined with the L-chain of a different clostridial neurotoxin. This hybrid, modified clostridial neurotoxin is then covalently linked, using linkages which may include one or more spacer regions, to a TM.

In another embodiment of the invention, the $H_N$ domain of a clostridial neurotoxin is combined with the L-chain of a different clostridial neurotoxin. This hybrid $LH_N$ is then covalently linked, using linkages which may include one or more spacer regions, to a TM. In a further embodiment of the invention, the light chain of a clostridial neurotoxin, or a fragment of the light chain containing the endopeptidase activity, is covalently linked, using linkages which may include one or more spacer regions, to a TM which can also effect the internalisation of the L-chain, or a fragment of the L-chain containing the endopeptidase activity, into the cytoplasm of the relevant secretory and/or neuronal cells in the airways responsible for secretion of mucus and or regulation of said secretion.

The agent is optionally expressed recombinantly as a fusion protein which includes an appropriate TM in addition to any desired spacer regions. The recombinantly expressed agent may be derived wholly from the gene encoding one serotype of neurotoxin or may be a chimaera derived from genes encoding one or more serotypes. In another embodiment of the invention the required $LH_N$, which may be a hybrid of an L and $H_N$ from different clostridial types, is expressed recombinantly as a fusion protein with the TM, and may include one or more spacer regions.

The light chain of a clostridial neurotoxin, or a fragment of the light chain containing the endopeptidase activity, may be expressed recombinantly as a fusion protein with a TM which can also effect the internalisation of the L-chain, or a fragment of the L-chain containing the endopeptidase activity, into the cytoplasm of the relevant secretory and or neuronal cells in the airways responsible for secretion of mucus and or regulation of said secretion. The expressed fusion protein may also include one or more spacer regions.

A neurotoxin fragment as described in the present invention can be prepared by methods well known in the protein art, including, but not limited to, proteolytic cleavage or by genetic engineering strategies. Said fragment is preferably a non-toxic fragment. The conjugation may be chemical in nature using chemical or covalent linkers. Conjugates according to the present invention may be prepared by conventional methods known in the art.

In a third aspect, the invention provides a composition for use in treating mucus hypersecretion, comprising:
  a compound according to any of the second aspect of the invention; and
  at least one of a pharmaceutically acceptable excipient, adjuvant and/or propellant,
  wherein the composition is for administration to the airways of a patient.

Aerosol administration is a preferred route of administration, though the present invention encompasses also any administration that delivers the compound to epithelia in the airways. Nasal administration is optional though buccal is preferred. The compound may thus be formulated for oral administration via aerosol or nebuliser or as a dry powder for inhalation using conventional excipients, adjuvants and/or propellants. The invention therefore further provides a pharmaceutical composition comprising a compound of the invention and a pharmaceutically acceptable canier.

In use the compound will generally be employed in a phannaceutical composition in association with a human pharmaceutical carrier, diluent and/or excipient, although the exact form of the composition will depend on the mode of administration. The compound may, for example, be employed in the form of an aerosol or nebulisable solution.

In a specific embodiment of the invention, described in further detail below, a polypeptide according to the invention comprises Substance P, and an L chain and a heavy chain $H_N$ region of botulinum toxin A. In use, this may be administered to a patient by aerosol. A solution of the polypeptide is prepared and converted into an aerosol using a nebuliser for inhalation into the lungs of nebulised particles of diameter 1-5 microns.

The dosage ranges for administration of the compounds of the present invention are those to produce the desired therapeutic effect. It will be appreciated that the dosage range required depends on the precise nature of the conjugate, the route of administration, the nature of the formulation, the age of the patient, the nature, extent or severity of the patient's condition, contraindications, if any, and the judgement of the attending physician. Wide variations in the required dosage, however, are to be expected depending on the precise nature of the conjugate. Variations in these dosage levels can be adjusted using standard empirical routines for optimisation, as is well understood in the art.

Fluid unit dosage forms are prepared utilising the compound and a pyrogen-free sterile vehicle. The compound, depending on the vehicle and concentration used, can be either dissolved or suspended in the vehicle. In preparing solutions the compound can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers maybe sterilised by autoclaving. Advantageously additives such as buffering, solubilising, stabilising, preservative or bactericidal, suspending or emulsifying agents and/or local anaesthetic agents may be dissolved in the vehicle.

Dry powders which are dissolved or suspended in a suitable vehicle prior to use may be prepared by filling presterilised drug substance and other ingredients into a sterile container using aseptic technique in a sterile area. Alternatively the drug and other ingredients may be dissolved into suitable containers using aseptic technique in a sterile area. The product is then freeze dried and the containers are sealed aseptically.

Compositions suitable for administration via the respiratory tract include aerosols, nebulisable solutions or microfine powders for insufflation. In the latter case, particle size of less than 50 microns, especially less than 10 microns, is preferred. Such compositions may be made up in a conventional manner and employed in conjunction with conventional administration devices.

In further aspects of the invention, there is provided use of a compound that inhibits exocytosis in mucus secreting cells or neurones that control or direct mucus secretion in manufacture of a medicament for treating mucus hypersecretion, asthma or COPD.

The invention yet further provides a method of manufacture of a pharmaceutical composition, comprising:
  obtaining a clostridial neurotoxin and modifying it so as to remove or disable its $H_C$ portion; or
  obtaining a clostridial neurotoxin the $H_C$ portion of which has been removed or disabled;
  linking the toxin with a targeting moiety that binds to (i) a mucus secreting cell, or (ii) a neuronal cell that controls or directs mucus secretion.

The invention still further provides a method of manufacture of a pharmaceutical composition, comprising obtaining a first component having the domains:
  an inhibiting domain which inhibits exocytosis in a mucus secreting cell or neuronal cell that controls or directs mucus secretion;
  a translocating domain which translocates the inhibiting domain into the cell; and
  linking the first component to a second component that binds to (i) a mucus secreting cell, or (ii) a neuronal cell that controls or directs mucus secretion.

The first and second components are preferably formulated in an orally administrable composition in combination with one or more or an excipient, an adjuvant and a propellant.

BRIEF DESCRIPTION OF THE DRAWINGS

Specific embodiments of the invention are now illustrated in the following examples with reference to the accompanying drawings in which.

EXAMPLES

Example 1

Method for the Preparation of Substance P-LHN/A Conjugates

The lyophilised peptide was rehydrated in 0.1% trifluoroacetic acid (TFA) to a final concentration of 10 mM. Aliquots of this solution were stored at −20 degrees C. until use. The $LH_N$/A was desalted into PBSE (PBS containing 1 mM EDTA). The resulting solution (3-5 mg/ml) was reacted with a three- or four-fold molar excess of SPDP by addition of a 10 mM stock solution of SPDP in DMSO. After 3 hours at room temperature the reaction was terminated by desalting over a PD-10 column into PBSE.

A portion of the derivatised $LH_N$/A was removed from the solution and reduced with DTT (5 mM, 30 min). This sample was analysed spectrophotometrically at 280 nm and 343 nm to determine the degree of derivatisation. The degree of derivatisation achieved was typically 2 mol/mol.

The bulk of the derivatised $LH_N$/A and the substance P peptide were mixed in proportions such that the peptide was in four-fold molar excess. The conjugation reaction was allowed to proceed for >16 hours at 4° C.

The product mixture was centrifuged to clear any precipitate that had developed. The supernatant was applied to a PD-10 column equilibrated in PBS and protein fractions were eluted by addition of PBS. Peptide and reaction by-products eluted after the main peak of protein and were discarded.

The conjugate mixture was concentrated to >1 mg/ml by centrifugation through concentrators (with 10000 molecular weight exclusion limit). The concentrated conjugate mixture was analysed by SDS-PAGE and Western blotting (probed with anti-substance P antibody) to confirm linkage of substance P peptide to $LH_N$/A.

The method described is for linkage of substance P peptide covalently to LH$_N$/A via a SPDP linker. A sulphydryl residue is incorporated into the C-terminus of the substance P residue, in this case by the addition of a Cys residue. Alternative linkers are available, including linkers utilising similar chemistry of derivatisation but generating non-reducible covalent bonds between the linked species.

The Substance P peptide sequence used in this particular example is RPKPQQFFGLMC (SEQ ID NO:2), though alternative sequences are also suitable, e.g. CRPKPQQFFGLM (SEQ ID NO:3), i.e. substance P with an N-terminal Cys.

The method described does not make use of any tagging system (e.g. poly His) to purify the conjugate from free $LH_N/A$. This has been demonstrated to be a successful method for the preparation of opioid peptide $LH_N/A$ such the receptor binding function of the peptide was not compromised. A similar approach can be applied to the synthesis of subP-$LH_N/A$.

FIG. 1 illustrates the preparation of the substance P-$LH_N/A$ conjugate of Example 1. In the results shown in FIG. 1, $LH_N/A$ and substance P-$LH_N/A$ samples at the concentrations indicated were applied to nitrocellulose and probed with rabbit anti-substance P antibody (upper two rows). The emergence of cross-reaction with the conjugate (second row), rather than the $LH_N/A$ (first row), is indicative of substance P conjugated to $LH_N/A$. The lower control row illustrates the presence of $LH_N/A$.

FIG. 2 shows Western blot detection of conjugated substance P-$LH_N/A$. Samples of substance P-$LH_N/A$ (lane 3) and $LH_N/A$ (lane 2) were electrophoresed alongside molecular weight markers (lane 1). Detection of substance P by rat anti-substance P antisera indicated protein of approx. 100 kDa molecular weight in the conjugate lane, but no such band in the $LH_N/A$ only lane. Thus the conjugated $LH_N/A$ does contain substance P.

Example 2

Method for the Preparation of a Broad Specificity Agent

Conjugation and purification of WGA-$LH_N/A$. WGA (10 mg/ml in phosphate-buffered saline (PBS)) was reacted with an equal concentration of SPDP (10 mM in dimethyl sulphoxide (DMSO)) for one hour at ambient temperature. Reaction by-products were removed by desalting into PBS prior to reduction of the cross-linker with dithiothreitol. The thiopyridone and DTT were then removed by desalting into PBS to result in derivatised WGA (dWGA) with 1 mole —SH incorporated per mole of WGA.

$LH_N/A$ at a concentration of 3-5mg/ml in PBSE (PBS containing 1 mM EDTA) was reacted with a three or four-fold molar excess of SPDP (10 mM in DMSO). After 3 h at ambient temperature the reaction was terminated by desalting over a PD-10 column into PBSE.

The derivatised WGA (dWGA) and the derivatised $LH_N/A$ (d$LH_N/A$) were mixed in a 3:1 molar ratio. After 16 h at 4° C. the mixture was centrifuged to clear any precipitate that had developed. The supernatant was concentrated by ultrafiltration before application to a Superose™ 12 column on an FPLC® chromatography system (Phamacia). The column was eluted with PBS and the fractions containing high molecular weight conjugate material (separated from free dWGA) were pooled and applied to PBS-washed N-acetylglucosamine-agarose (GlcNAc-agarose). WGA-$LH_N/A$ conjugate bound to the GlcNAc-agarose and was eluted from the column by the addition of 0.3 M N-acetylglucosamine in PBS. The elution profile was followed at 280 nm and fractions containing conjugate were pooled, dialysed against PBS, and stored at 4° C. until use.

FIG. 3 shows SDS-PAGE analysis of WGA-$LH_N/A$ purification scheme. Protein fractions were subjected to 4-20% polyacrylamide SDS-PAGE prior to staining with Coomassie blue. Lanes 6-8 were run in the presence of 0.1 M DTT. Lanes 1 (&7) and 2 (& 8) represent derivatised WGA and derivatised $LH_N/A$ respectively. Lanes 3-5 represent conjugation mixture, post-Superose-12 chromatography and post GlcNAc-affinity chromatography respectively. Lanes 6 represents a sample of reduced final material. Approximate molecular masses (kDa) are indicated on the Figure.

Example 3

Preparation and Maintenance of Neuronal Cultures and Inhibition of Neurotransmitter Release PC12 cells were seeded at a density of $4\times10^5$ cells/well onto 24 well (matrigel coated) plates (NUNC™) from stocks grown in suspension. The cells were cultured for 1 week prior to use in RPMI, 10% horse serum, 5% foetal bovine serum, 1% L-glutamine. SH-SY5Y cells were seeded at a density of $5\times10^5$ cells/well onto 24 well plates (FALCON™). The cells were cultured in HAM-F12:MEM (1:1 v/v), 15% foetal bovine serum, 1% MEM non-essential amino acids, 2 mM L-glutamine for 1 week prior to use. Embryonic spinal cord (eSC) neurons were prepared from spinal cords dissected from 14-15 day old foetal Sprague Dawley rats and were used after 21 days in culture using a modification of previously described method.

Inhibition of transmitter release. PC12 cells or SH-SY5Y cells were washed with a balanced salt solution (BSS:137 mM NaCl, 5 mM KCl, 2 mM $CaCl_2$, 4.2 mM $NaHCO_3$, 1.2 mM $MgCl_2$, 0.44 mM $KH_2PO_4$, 5 mM glucose, 20 mM HEPES, pH7.4) and loaded for 1 hour with [$^3$H]-noradrenaline (2 μCi/ml, 0.5 ml/well) in BSS containing 0.2 mM ascorbic acid and 0.2 mM pargyline. Cells were washed 4 times (at 15 minutes intervals for 1 hour) then basal release determined by a 5 minute incubation with BSS (5 mM $K^+$). Cells were then depolarised with 100 mM $K^+$ (BSS with $Na^+$ reduced accordingly) for 5 minutes to determine stimulated release. Superfusate (0.5 ml) was removed to tubes on ice and briefly centrifuged to pellet any detached cells. Adherent cells were solubilised in 2 M acetic acid/0.1% trifluoroacetic acid (250 μl/well). The quantity of released and non-released radio label was determined by liquid scintillation counting of cleared superfusates and cell lysates respectively. Total uptake was calculated by addition of released and retained radioactivity and the percentage release calculated ((released counts/total uptake counts) x100).

eSC neurons were loaded with [$^3$H]-glycine for 30 minutes prior to determination of basal and potassium-stimulated release of transmitter. A sample of 0.2 M NaOH-lysed cells was used to determine total counts, from which % release could be calculated.

FIGS. 4-6 show inhibition of neurotransmitter release from cultured neuronal cells. PC12 (FIG. 4), SH-SY5Y cells (FIG. 5) and eSC neurons (FIG. 6) exposed for three days to a range of concentrations of WGA-$LH_N/A$ (filled symbols) and $LH_N/A$ (open symbols) were assessed for stimulated [$^3$H]-noradrenaline release (SH-SY5Y and PC12 cells) or [$^3$H]-glycine release (eSC) capability. Results are expressed as percentage inhibition compared to untreated controls. Each concentration was assessed in triplicate. For each cell type the dose response curve is representative of at least three experiments. Each point shown is the mean of at least three determinations±SE of the mean.

Figure 1:
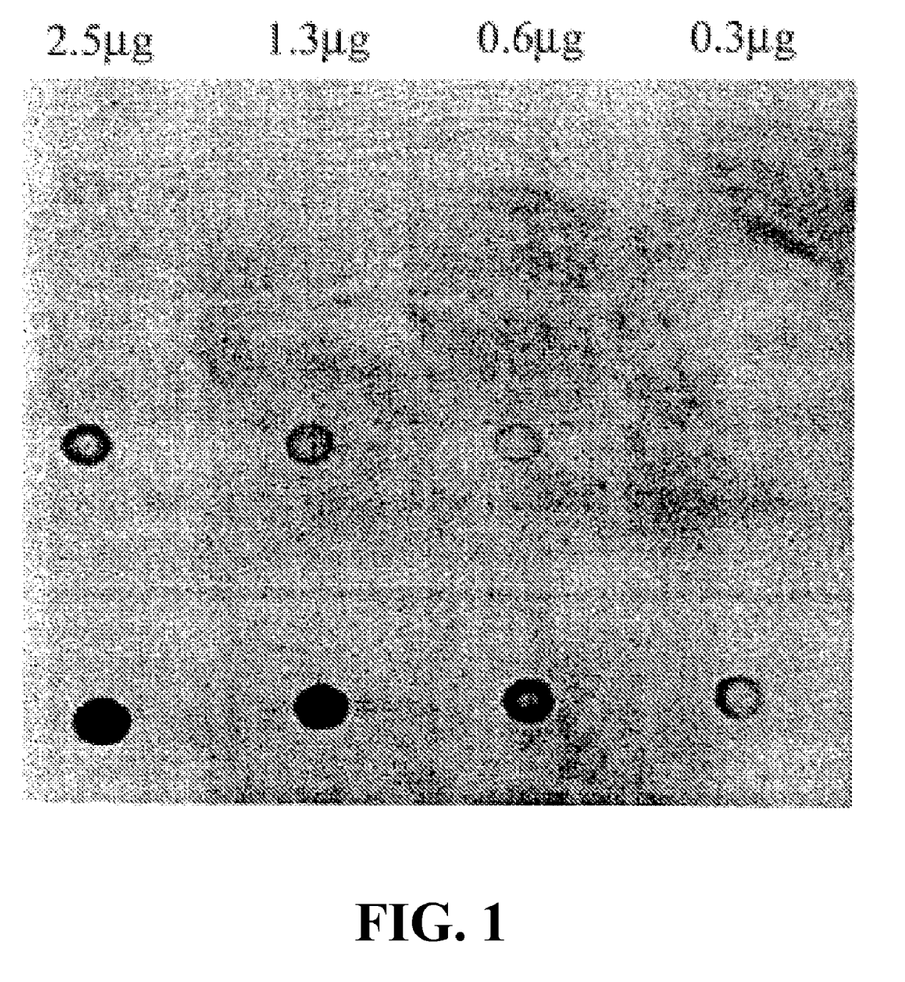
FIG. 1 illustrates the preparation of the substance P-$LH_N$/A conjugate of Example 1.
Figure 2:
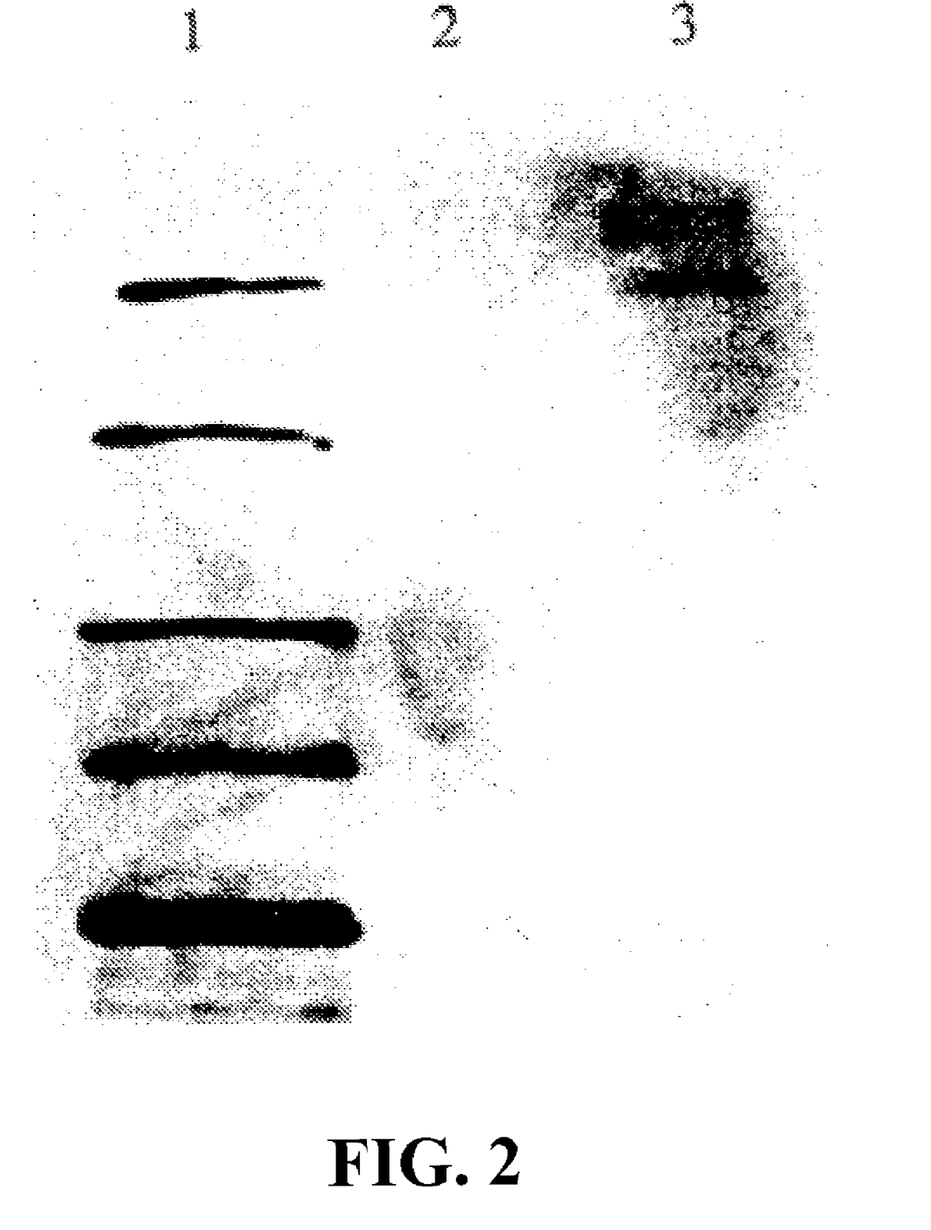
FIG. 2 shows Western blot detection of conjugated substance P-$LH_N$/A.
Figure 3:
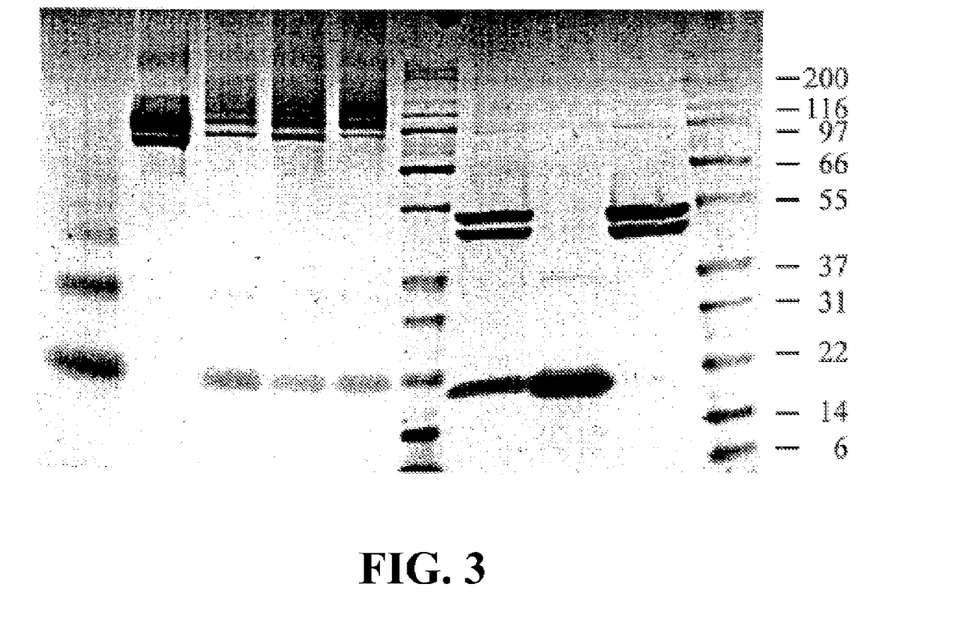
FIG. 3 shows SDS-PAGE analysis of a WGA-$LH_N$/A purification scheme.
Figure 4:
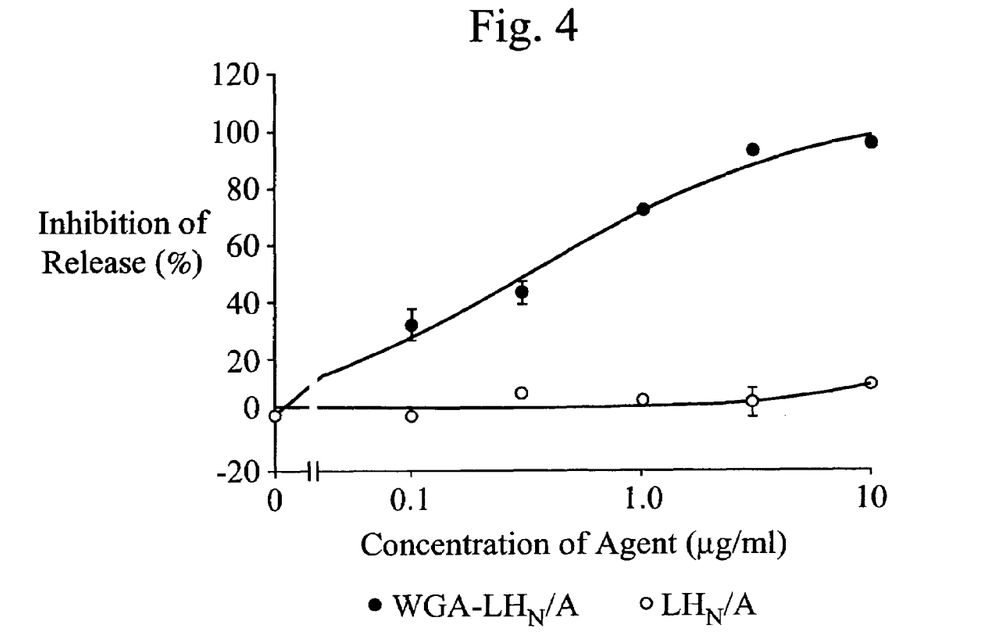
FIGS. 4-6 show inhibition of neurotransmitter release from cultured neuronal cells.
Figure 5:
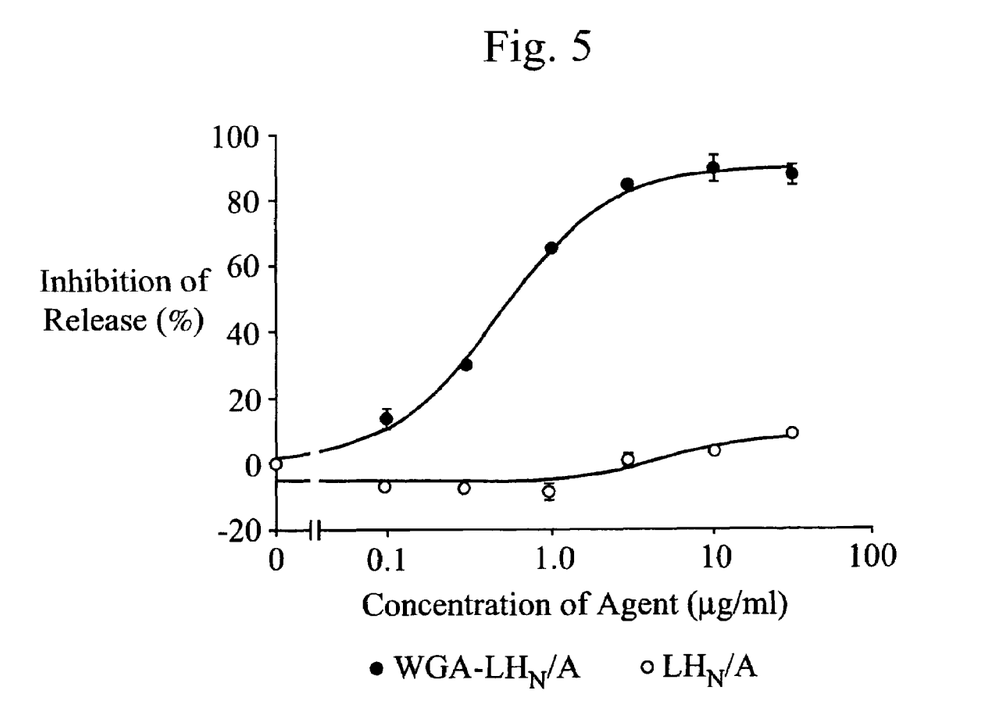
Figure 6:
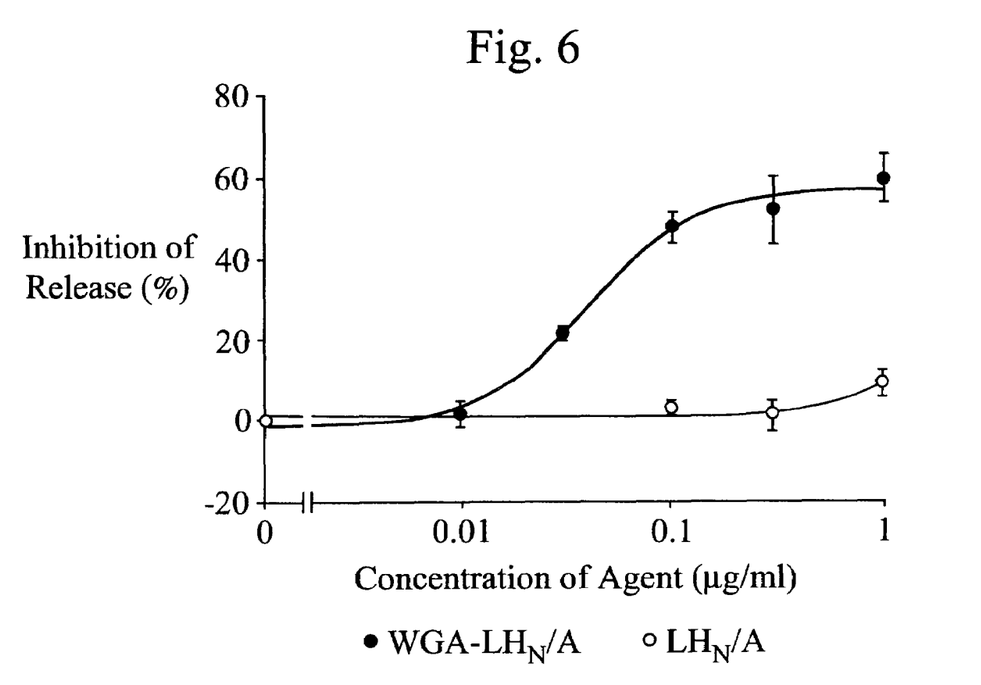
Figure 7:
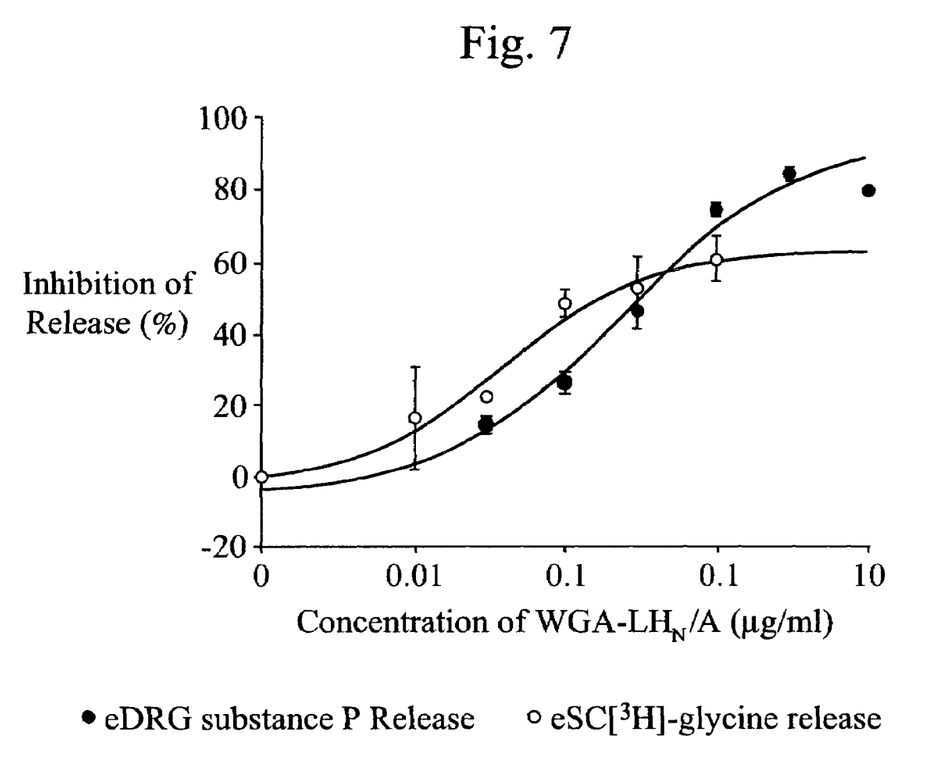
FIG. 7 shows WGA-$LH_N$/A inhibits release from, but does not have specificity for, eDRG neurons.

FIG. 7 shows dose-response curves of WGA-LH$_N$/A inhibition of eDRG substance P and eSC [$^3$H]-glycine release. Cells were exposed to conjugate for three days. Representative curves are shown. Mean IC$_{50}$eDRG:0.32+0.05 μg/ml (n=4), eSC:0.06±0.01 μg/ml (n=3).

Example 4

Method for the Preparation of LC/B-epidermal Growth Factor with a Translocation Domain from Diphtheria Toxin by Recombinant Expression Using standard DNA manipulation procedures, the DNA encoding LC/B, diphtheria toxin amino acids 194-380, and epidermal growth factor are assembled in frame and inserted into an appropriate expression vector. Inserted between the LC/B DNA and the diphtheria toxin translocation domain is DNA encoding a short spacer sequence with a specific cleavable peptide bond (↓), bounded by a pair of cysteine amino acids. Examples of specific enzymes that may be used to activate the fusion protein include factor Xa (IEGR↓) (SEQ ID NO:4), enterokinase (DDDDK↓) (SEQ ID NO:5), TEV protease (EXXYXQS↓G) (SEQ ID NO:6), precission (LEVLFQ↓GP) (SEQ ID NO:7), Thrombin (LVPR↓GS) (SEQ ID NO:8) and genenase (HY or YH). Expression of a single polypeptide of the form LC/B-DT$_{194-380}$-EGF is achieved in *E. coli* using standard techniques. The expressed fusion protein is isolated from *E. coli* by standard purification techniques and cleaved by the specific activation enzyme prior to assessment in an in vitro cell model.

Example 5

Method for the Preparation of LC/C-epidermal Growth Factor with a Translocation Domain from Pseudomonas Exotoxin by Recombinant Expression Using standard DNA manipulation procedures, the DNA encoding LC/C, pseudomonas exotoxin amino acids 405-613, and epidermal growth factor are assembled in frame and inserted into an appropriate expression vector. Inserted between the LC/C DNA and the pseudomonas exotoxin translocation domain is DNA encoding a short spacer sequence with a specific cleavable peptide bond, bounded by a pair of cysteine amino acids. Examples of specific enzymes that may be used to activate the fusion protein include factor Xa (IEGR↓), (SEQ ID NO:4), enterokinase (DDDDK↓) (SEQ ID NO:5), TEV protease (EXXYXQS↓G) (SEQ ID NO:6), precission (LEVLFQ↓GP) (SEQ ID NO:7), Thrombin (LVPR↓GS) (SEQ ID NO:8) and genenase (HY or YH). Expression of a single polypeptide of the form LC/C-PE$_{405-613}$-EGF is achieved in *E. coli* using standard techniques. The expressed fusion protein is isolated from *E. coli* by standard purification techniques and cleaved by the specific activation enzyme prior to assessment in an in vitro cell model.

Example 6

Method for the Preparation of LC/A-epidermal Growth Factor with a Translocation Domain from Influenza Virus Haemagglutinin by Recombinant Expression Using standard DNA manipulation procedures, the DNA encoding LC/A, GLFGAIAGFIENGWEGMIDGWYG (SEQ ID NO:1) from influenza virus haemagglutinin (HA), and epidermal growth factor are assembled in frame and inserted into an appropriate expression vector. Inserted between the LC/A DNA and the haemagglutinin sequence is DNA encoding a short spacer sequence with a specific cleavable peptide bond, bounded by a pair of cysteine amino acids. Examples of specific enzymes that may be used to activate the fusion protein include factor Xa (IEGR↓) (SEQ ID NO:4), enterokinase (DDDDK↓) (SEQ ID NO:5), TEV protease (EXXYXQS↓G) (SEQ ID NO:6), precission (LEVLFQ↓GP) (SEQ ID NO:7), Thrombin (LVPR↓GS) (SEQ ID NO:8) and genenase (HY or YH). Expression of a single polypeptide of the form LC/A-HA-EGF is achieved in *E. coli* using standard techniques. The expressed fusion protein is isolated from *E. coli* by standard purification techniques and cleaved by the specific activation enzyme prior to assessment in an in vitro cell model.

The agent described in this invention can be used in vivo, either directly or as a pharmaceutically acceptable salt, for the treatment of conditions involving mucus hypersecretion, including COPD and asthma.

What is claimed is:

1. A method of treating hypersecretion of mucus, comprising administering, topically to the airways of a patient in need thereof, a therapeutically effective amount of a compound, said compound comprising:
   (a) a light chain(L-chain) or L-chain fragment of a clostridial neurotoxin, which L-chain or L-chain fragment includes the active proteolytic enzyme domain of the L-chain;
   (b) a targeting domain that binds to a target cell selected from the group consisting of (i) a mucus secreting cell, and (ii) a neuronal cell controlling or directing mucus secretion; and
   (c) a translocating domain that translocates the L-chain or L-chain fragment into the target cell, wherein said translocating domain is a translocating domain of a bacterial or viral protein;
   with the proviso that said compound is not a botulinum toxin; and wherein, following administration to said patient, the compound binds to and delivers the L-chain or L-chain fragment into said target cell, thereby (i) inhibiting mucus secretion by mucus secreting cells, (ii) inhibiting neurotransmitter release from neuronal cells controlling or directing mucus secretion, or (iii) inhibiting mucus secretion by mucus secreting cells and inhibiting neurotransmitter release from neuronal cells controlling or directing mucus secretion.

2. A method according to claim 1, wherein said translocating domain is a translocating domain of a bacterial toxin, or a translocating domain of a virally expressed membrane fusion protein.

3. The method of claim 1, wherein the translocating domain is selected from the group consisting of a translocating domain of clostridial neurotoxin, a translocating domain of diphtheria toxin, domain II of pseudomonas exotoxin A, a translocating domain of influenza virus haemagglutinin, a translocating domain of a fiasogenic protein of Semliki Forest virus, a translocating domain of vesicular stomatitis virus glycoprotein G, a translocating domain of SER virus F protein and a translocating domain of Foamy virus envelope glycoprotein.

4. A method according to claim 1, wherein the targeting domain is a domain selected from the group consisting of Substance P, vasoactive intestinal polypeptide (VIP), beta$_2$ adrenoreceptor agonists, gastrin releasing peptide, and calcitonin gene related peptide.

5. A method according to claim 1, wherein said targeting domain binds to a target cell selected from the group consisting of epithelial goblet cells, submucosal gland mucus-secreting cells, Clara cells, serous cells, sensory efferent C-fibres, and Non-adrenergic Non-Cholinergic neural system fibres.

6. A method of treating chronic obstructive pulmonary disease (COPD), comprising administering, topically to the airways of a patient in need thereof, a therapeutically effective amount of a compound, said compound comprising:
   (a) a light chain (L-chain) or L-chain fragment of a clostridial neurotoxin, which L-chain or L-chain fragment includes the active proteolytic enzyme domain of the L-chain;
   (b) a targeting domain that binds to a target cell selected from the group consisting of (i) a mucus secreting cell, and (ii) a neuronal cell controlling or directing mucus secretion; and (c) a translocating domain that translocates the L-chain or L-chain fragment into the target cell, wherein said translocating domain is a translocating domain of a bacterial or viral protein;

with the proviso that said compound is not a botulinum toxin; and wherein following administration to said patient the compound binds to and delivers the L-chain or L-chain fragment into said target cell, thereby (i) inhibiting mucus secretion by mucus secreting cells, (ii) inhibiting neurotransmitter release from neuronal cells controlling or directing mucus secretion, or (iii) inhibiting mucus secretion by mucus secreting cells and inhibiting neurotransmitter release from neuronal cells controlling or directing mucus secretion.

7. A method according to claim 6, wherein said translocating domain is a translocating domain of a bacterial toxin, or a translocating domain of a virally expressed membrane fusion protein.

8. A method according to claim 6, wherein said translocating domain is selected from the group consisting of a translocating domain of diphtheria toxin, domain II of pseudomonas exotoxin A, a translocating domain of influenza virus haemagglutinin, a translocating domain of a fusogenic protein of Semliki Forest virus, a translocating domain of vesicular stomatitis virus glycoprotein G, a translocating domain of SER virus F protein and a translocating domain of Foamy virus envelope glycoprotein.

9. A method according to claim 6, wherein the targeting domain is a domain selected from the group consisting of Substance P, VIP, beta$_2$ adrenoreceptor agonists, gastrin releasing peptide, and calcitonin gene related peptide.

10. A method according to claim 6, wherein said targeting domain selectively binds to a target cell selected from the group consisting of epithelial goblet cells, submucosal gland mucus-secreting cells, Clara cells, and serous cells.

11. A method for treating asthma, comprising administering, topically to the airways of a patient in need thereof, a therapeutically effective amount of a compound, said compound comprising:
(a) a light chain (L-chain) or L-chain fragment of a clostridial neurotoxin, which L-chain or L-chain fragment includes the active proteolytic enzyme domain of the L-chain;
(b) a targeting domain that binds to a target cell selected from the group consisting of (i) a mucus secreting cell, and (ii) a neuronal cell controlling or directing mucus secretion; and
(c) a translocating domain that translocates the L-chain or L-chain fragment into the target cell, wherein said translocating domain is a translocating domain of a bacterial or viral protein;
with the proviso that said compound is not a botulinum toxin; and wherein following administration to said patient the compound binds to and delivers the L-chain or L-chain fragment into said target cell, thereby (i) inhibiting mucus secretion by mucus secreting cells, (ii) inhibiting neurotransmitter release from neuronal cells controlling or directing mucus secretion, or (iii) inhibiting mucus secretion by mucus secreting cells and inhibiting neurotransmitter release from neuronal cells controlling or directing mucus secretion.

12. A method according to claim 11, wherein said translocating domain is a translocating domain of a bacterial toxin, or a translocating domain of a virally expressed membrane fusion protein.

13. A method according to claim 11, wherein said translocating domain is selected from the group consisting of a translocating domain of diphtheria toxin, domain II of pseudomonas exotoxin A, a translocating domain of influenza virus haemagglutinin, a translocating domain of a fusogenic protein of Semliki Forest virus, a translocating domain of vesicular stomatitis virus glycoprotein G, a translocating domain of SER virus F protein and a translocating domain of Foamy virus envelope glycoprotein.

14. A method according to claim 11, wherein the targeting domain is a domain selected from the group consisting of Substance P, VIP, beta$_2$ adrenoreceptor agonists, gastrin releasing peptide, and calcitonin gene related peptide.

15. A method according to claim 11, wherein said targeting domain selectively binds to a target cell selected from the group consisting of epithelial goblet cells, submucosal gland mucus-secreting cells, Clara cells, and serous cells.

16. A compound comprising:
(a) a light chain (L-chain) or L-chain fragment of a clostridial neurotoxin, which L-chain or L-chain fragment includes the active proteolytic enzyme domain of the L-chain;
(b) a targeting domain that binds to a target cell selected from the group consisting of (i) a mucus secreting cell, and (ii) a neuronal cell controlling or directing mucus secretion; and
(c) a translocating domain that translocates the L-chain or L-chain fragment into the target cell, wherein said translocating domain is a translocating domain of a bacterial or viral protein;
with the proviso that said compound is not a botulinum toxin; and
wherein the compound binds to and delivers the L-chain or L-chain fragment into said target cell, thereby (i) inhibiting mucus secretion by mucus secreting cells, (ii) inhibiting neurotransmitter release from neuronal cells controlling or directing mucus secretion, or (iii) inhibiting mucus secretion by mucus secreting cells and inhibiting neurotransmitter release from neuronal cells controlling or directing mucus secretion.

17. The compound of claim 16, wherein said translocating domain is a translocating domain of a bacterial toxin, or a translocating domain of a virally expressed membrane fusion protein.

18. The compound of claim 16, wherein the translocating domain is selected from the group consisting of: a translocating domain of clostridial neurotoxin, a translocating domain of diphtheria toxin, domain II of pseudomonas exotoxin A, a translocating domain of influenza virus haemagglutinin, a translocating domain of a fusogenic protein of Semliki Forest virus, a translocating domain of vesicular stomatitis virus glycoprotein G, a translocating domain of SER virus F protein and a translocating domain of Foamy virus envelope glycoprotein.

19. The compound of claim 16, wherein the targeting domain is a domain selected from the group consisting of Substance P, vasoactive intestinal polypeptide (VIP), beta$_2$ adrenoreceptor agonists, gastrin releasing peptide, and calcitonin gene related peptide.

20. The compound of claim 16, wherein the targeting domain binds to a target cell selected from the group consisting of epithelial goblet cells, submucosal gland mucus-secreting cells, Clara cells, serous cells, sensory efferent C-fibres, and Non-adrenergic Non-Cholinergic neural system fibres.

21. The compound of claim 16, wherein the targeting domain binds to a target cell selected from the group consisting of epithelial goblet cells, submucosal gland mucus-secreting cells, Clara cells and serous cells.

* * * * *